(12) United States Patent
Dilkes et al.

(10) Patent No.: US 10,595,479 B2
(45) Date of Patent: Mar. 24, 2020

(54) INDUCED MUTAGENESIS

(71) Applicant: Purdue Research Foundation, West Lafayette, IN (US)

(72) Inventors: Brian Dilkes, Lafayette, IN (US); Gurmukh S. Johal, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/305,709

(22) PCT Filed: Apr. 24, 2015

(86) PCT No.: PCT/US2015/027623
§ 371 (c)(1),
(2) Date: Oct. 21, 2016

(87) PCT Pub. No.: WO2015/164805
PCT Pub. Date: Oct. 29, 2015

(65) Prior Publication Data
US 2017/0042103 A1    Feb. 16, 2017

Related U.S. Application Data

(60) Provisional application No. 61/983,708, filed on Apr. 24, 2014.

(51) Int. Cl.
*A01H 1/06*      (2006.01)
(52) U.S. Cl.
CPC ..................................... *A01H 1/06* (2013.01)
(58) Field of Classification Search
None
See application file for complete search history.

(56) References Cited

U.S. PATENT DOCUMENTS

| | | | |
|---|---|---|---|
| 6,770,801 B2 * | 8/2004 | Leto .......................... | A01H 5/10 800/264 |
| 2010/0212043 A1 * | 8/2010 | Stuurman ................ | A01H 1/04 800/260 |

OTHER PUBLICATIONS

Roig et al., 2004, Genetics 167: 439-448.*
Neuffer et al., 2009, In: J.L. Bennetzeu and S. Hake (eds.), Maize Handbook—vol. II: Genetic and Genomics, Springer Science + Business Media, pp. 63-84.*
Till et al., 2004, BMC Plant Biology 4:12, pp. 1-8.*
Chaikam et al., 2011, Theor. Appl. Genet. 123: 985-997.*
Dollinger, 1954, Genetics 39: 750-766.*
Wang et al., 2009, Generation of new rice cultivars from mature pollen treated with gamma-radiation, In: Induced Mutations in the Genomic Era, Q.Y. Shu, ed., FAO, Rome, pp. 231-234.*

* cited by examiner

*Primary Examiner* — Bratislav Stankovic
(74) *Attorney, Agent, or Firm* — Purdue Research Foundation; Liang Zeng Yan

(57) ABSTRACT

Presented herein are methods for creating a desired genetic variant at a high efficiency from a seed. In one aspect, a method for creating a desired genetic variant at a high efficiency from a seed is presented. The method involves subjecting isolated pollen to a chemical mutagen to produce a first generation seed, planting the first generation seed in (n) plots to produce first generation plants, recovering mutagenized pollen from the first generation plants, pollinating a female parent with the recovered mutagenized pollen to produce a next generation seed, subjecting pollen from the next generation seed to mutagenesis to pollinate the first generation plant, resulting in a new next generation seed, planting the new next generation seed to produce a new next generation plant, and subjecting pollen from the new next generation plant to mutagenesis to pollinate the new next generation plant.

3 Claims, 11 Drawing Sheets

INDUCED MUTAGENESIS

CROSS-REFERENCE TO RELATED APPLICATIONS

The present non-provisional patent application is a national stage entry under 35 U.S.C. § 371(b) of International Application No. PCT/US2015/027623, filed on Apr. 24, 2015, which claims priority under 35 U.S.C. § 119(e) to U.S. Provisional Patent Application Ser. No. 61/983,708, filed on Apr. 24, 2014, the contents of which are hereby incorporated by reference in its entirety into this disclosure.

TECHNICAL FIELD

The present disclosure generally relates to gene sequencing, and in particular to mutagenesis.

BACKGROUND

Among the most effective ways to assign functions to genes is by having genetic variants of the gene in question. Such genetic variants can be of natural origin or generated deliberately by mutagenesis. The effectiveness and use of induced mutagenesis depends a great deal on the mutation efficiency of the reagent and/or the procedure. Various forms or reagents to intentionally induce mutations in plants exist, but chemical mutagenesis by ethyl methanesulfonate (EMS), an inducer of point mutations in DNA, has gained interest. EMS is an alkylating agent that reacts mainly with the guanine (G) base in the DNA to change it to O-6-ethylguanine, which prefers to base pair with adenine (A) during DNA replication instead of its natural partner, the cytosine (C). As a result, an A is introduced at the location in the DNA where there was a C before. Because the new A will naturally hydrogen bond with thymine (T) during further rounds of DNA replication, the original GC base pair is converted into an AT base pair transition when mutagenesis is done with EMS.

Seed mutagenesis is the method of choice in almost all plant species except maize, where EMS mutagenesis is done via pollen. The main reason for this is that maize is a monoecious plant with separate male and female inflorescences at two separate locations on the plant. The male flowers are present only in the tassel, which forms at the top of the main axis of the plant, and the female flowers are present in the ear, which is a modified lateral shoot on the side of the main axis approximately 5-6 leaves below the tassel node. The maize embryonic cells that eventually morph into the tassel or the ear are already split into separate lineages by the time the maize kernels (seed) mature. When the maize seed is treated with EMS, the mutations that are generated in the ear primordial cells are completely independent from the mutations that are induced in the tassel primordial cells. To get these mutations in homozygous condition, which is absolutely needed to reveal recessive mutations, the M3 generation in maize is of interest because even when M1 plants (derived from EMS treated seed) are self-fertilized to produce the M2 progeny, the ear and tassel mutations are consolidated together in a heterozygous condition. This reproductive peculiarity of maize also causes the original germ line mutations to be amplified enormously, especially via the pollen, imposing serious limitations on the recovery and genetic interpretation of most mutations.

To eliminate these problems with seed mutagenesis, as well as to avoid the tremendous amount of work and expense that goes with having to raise an extra generation to recover mutant phenotypes (propagating thousands of plants, especially by self-pollination, is not trivial), a pollen mutagenesis protocol involving EMS was developed. In addition to allowing the revelation of dominant mutants in the M1 generation and recessive mutations in the M2 generation, this pollen mutagenesis protocol generates mutations that are independent of each other. An additional advantage of mutagenesis via pollen is that it allows one to conduct targeted mutant screens (also known as non-complementation screens) to specifically generate a series of mutations in a gene of interest, for example screening for non-complementation of a recessive mutation.

One disadvantage of pollen mutagenesis, which has been optimized to work only in maize thus far, is its mutation efficiency. It is about one out of 1,000 gametes treated with EMS, when gauged by functional genetic tests. When tested molecularly, the density of mutations caused by the pollen EMS protocol in maize was found to be about 2 mutations per Mb of DNA. Whatever the reasons, the relatively low mutation frequency of mutagenesis in this protocol acts as a deterrent for many working either in the public or commercial sector. This impediment can be eliminated if the mutation frequency is enhanced.

There is therefore an unmet need for a cost-effective, high accuracy method for generating independent mutant alleles.

SUMMARY

In one aspect, a method for creating a desired genetic variant at a high efficiency from a seed is presented. The method involves subjecting isolated pollen to a chemical mutagen to produce a first generation seed, planting the first generation seed in (n) plots to produce first generation plants, recovering mutagenized pollen from the first generation plants, pollinating a female parent with the recovered mutagenized pollen to produce a next generation seed, subjecting pollen from the next generation seed to mutagenesis to pollinate the first generation plant, resulting in a new next generation seed, planting the new next generation seed to produce a new next generation plant, and subjecting pollen from the new next generation plant to mutagenesis to pollinate the new next generation plant. This method can be repeated until the desired genetic variant is obtained.

In yet another aspect, the method further includes planting seeds from a desired generational lot and allowing for self-pollination to occur resulting in the production of BC(n)M(n+1)S1 families. A reagent to impair DNA repair can be used. The reagent to impair DNA repair acts as an inhibitor of base excision repair. The reagent to impair DNA repair can be 7-Nitroindole-2-carboxylic acid. The method results in a yield of highly mutated seeds.

In yet another aspect, a method is presented for creating a desired genetic variant at a high efficiency from a seed, involving obtaining at least one seed, treating the at least one seed with a mutagen to result in at least one treated seed, planting the at least one treated seed to result in at least one first-generation plant, pollinating the at least one plant in a combination to produce at least one next-generation seed, treating the at least one next generation seed with a mutagen to result in at least one treated next-generation seed, planting the at least one treated next-generation seed to produce at least one next-generation plant; and pollinating the next-generation plants to thereby create the desired genetic variant. Such a method can further involve planting the next-generation seed in a setting different from the first-generation seed. In addition, adding a pollen EMS treatment to the first-generation plant can be involved. Further, a pollen EMS treatment can be added to the next-generation plant.

The herein disclosed methods can further involve the mutagen being a combination of mutagens. Moreover, the mutagen used to treat the at least one next-generation seed is the same as the mutagen used to create the at least one first-generation seed.

In another aspect, the pollen is mutagenized with a chemical mutagen. In some aspects, the chemical mutagen is ethyl methanesulfonate (EMS). The female parent can be mutagenized with EMS. The chemical mutagen can also be any one of, or a combination of, N-ethyl-N-nitrsourea, nitrosyl methyl urea, methyl methanosulfonate, ethidium bromide, psoralen, acridine orange, and sodium azide. The mutagen can also include a physical agent, such as any one of or a combination of fast neutrons, gamma rays, x-rays, and ultra-violet light.

In yet another aspect, the seeds are from any one of or a combination of a polyploidy crop and a cereal crop. The polyploidy crop can be, but is not limited to, any one of or a combination of any one of wheat, barley, soybean, cotton, oat, rice, sugarcane, maize, tomato, watermelon, sugar beet, and cassava.

DETAILED DESCRIPTION

Figure 1:
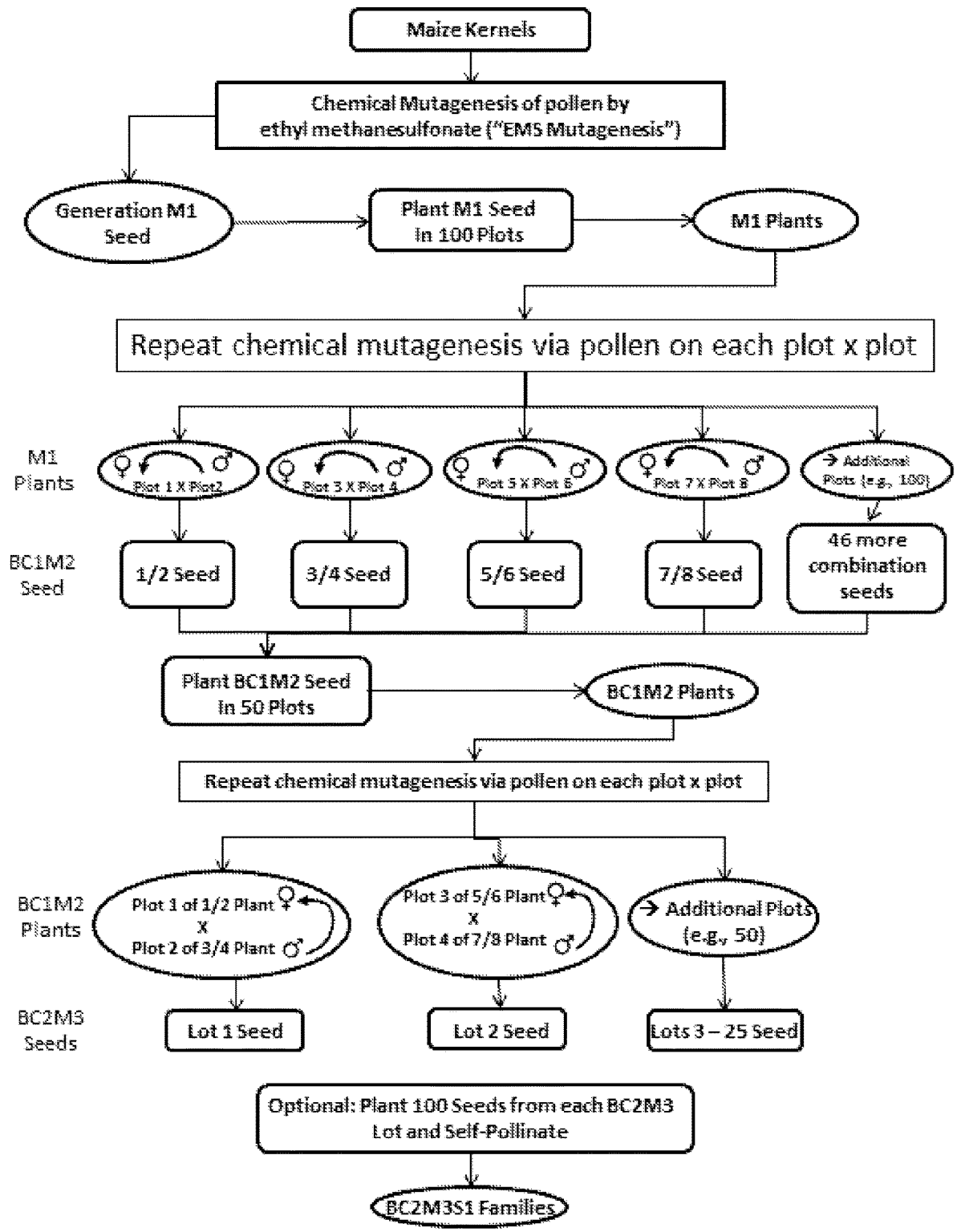
FIG. 1 is a process flow of the steps of an embodiment of the disclosed method.

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Disclosed herein is a novel method of creating new variation at a high efficiency by mutagenesis which holds great promise not only for defining gene function but also in the area of new gene discovery. In addition, it provides novel genetic variation capable of boosting crop breeding and productivity.

The herein disclosed method, which enhances the frequency of mutagenesis (as an exemplary embodiment, ethyl methanesulfonate (EMS) mutations) in maize by several folds, involves conducting pollen EMS mutagenesis not only once but many times, generation after generation. It should be noted that as used herein, "mutagenesis" and "chemical mutagenesis" are used interchangeably. A key requirement or design of the method is to keep the mutations independent of each other and also in heterozygous condition throughout the procedure.

Figure 2A:
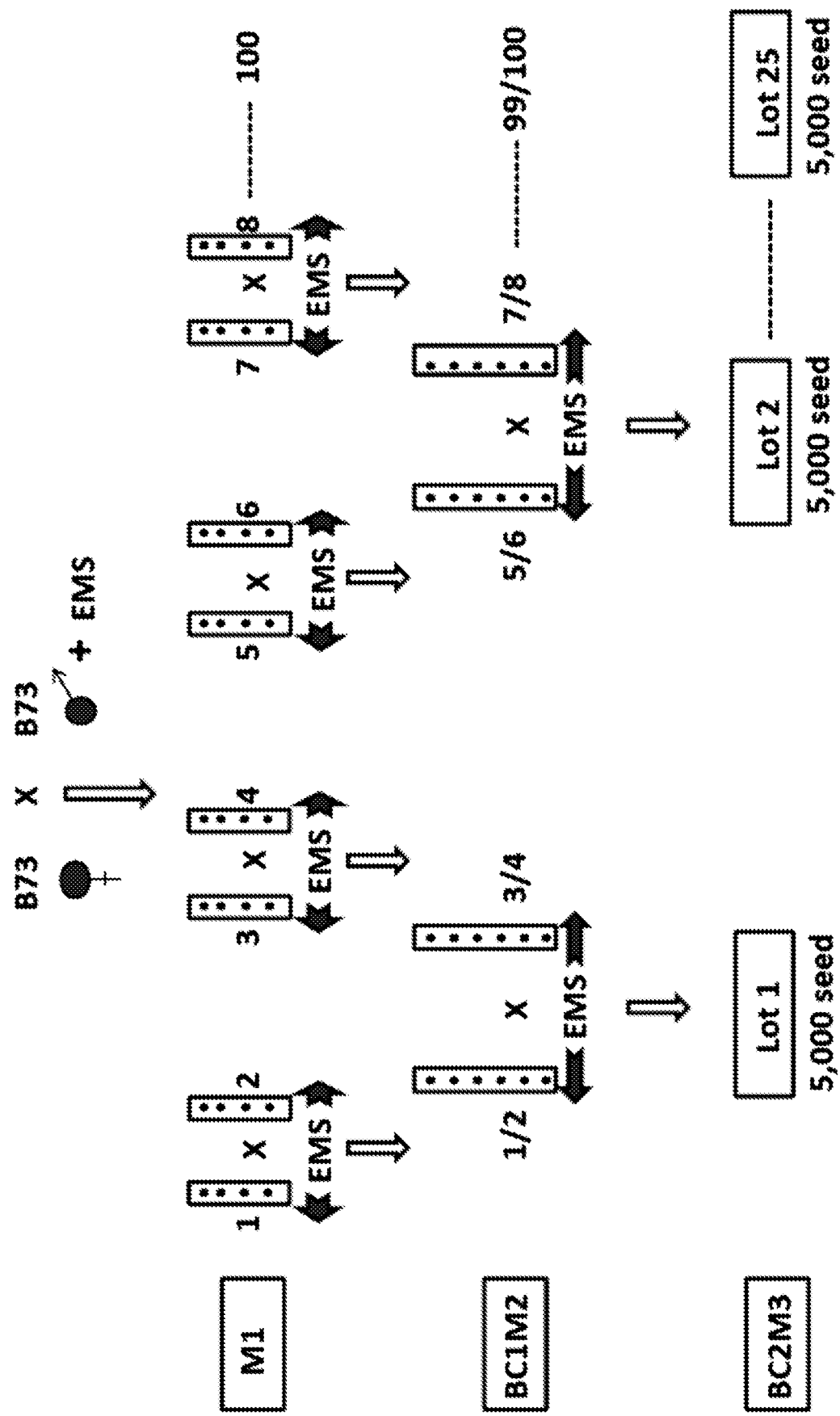
FIG. 2a is a plot showing mutagenesis using a chemical mutagen.
Figure 2B:
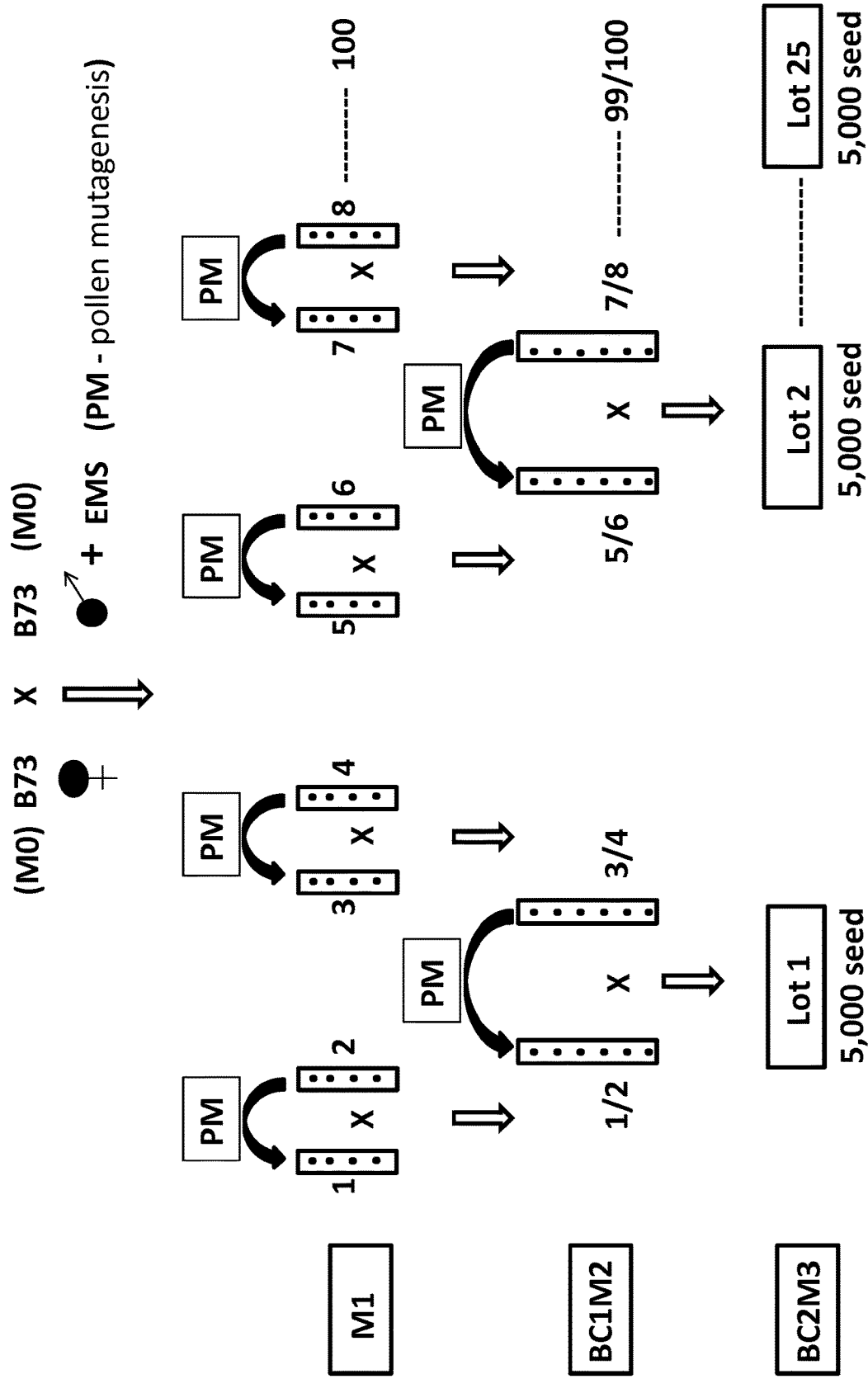
FIG. 2b is a plot showing mutagenesis using a chemical mutagen.

FIG. 1 illustrates an embodiment of the process flow of the steps of the disclosed method, the steps of which are outlined in more detail below. First, EMS mutagenesis is conducted using the traditional pollen treatment protocol. M1 plants are then planted in multiple plots/rows (for example, 100) with 10 kernels each (it can be more or less than 10; the number 10 is used herein as an example only). Then repeat pollen EMS mutagenesis with M1 plants but by restricting pollinations in pair-wise combinations so as to keep the mutations induced at the M2 level independent of the mutations coming from M1 generation (FIGS. 2a and 2b). This is accomplished by taking pollen from M1 plants of one plot (plot 2, for example) and using it to pollinate ears of the adjacent plot (plot 1) after treating with EMS. Similarly, pollen from plot 4 plants is to be onto ears of plot 3, from plot 6 onto 5, and so on. The BC1M2 seed thus produced will come from 50 plots, plots 1, 3, 5, . . . , and 99. This generates 50 lots of the BC1M2 seed with each lot containing independent mutations caused by two successive rounds of EMS mutagenesis. It should be appreciated that although in FIG. 1 the male is being EMS mutagenized, and then being used to pollinate the female, the reciprocal cross is also possible.

Next, the BC1M2 seed is planted in 50 plots, with seeds of each BC1M2 lot being planted in separate plot. A plot can be of a single long row or a number of rows so that 100 BC1M2 plants are there in each of the 50 plots. Another round of pollen EMS mutagenesis is conducted but again in paired plots. For example, treat pollen of plot 2 with EMS and use it to pollinate ears on plot 1, so on and so forth as before (FIGS. 2a and 2b). This results in 25 separate lots or batches of the BC2M3 seed, again each containing all independent mutations in a heterozygous condition. The iterative mutagenesis can end here and these plots can be selfed to generate large amounts of the BC2M3 seed per lot (for example, 5,000 per BC2M3 lot). For purposes of this disclosure, the word "selfed" as used herein means "self-pollinated," which is to mean the act of self-pollination. This is not the only option. Another embodiment involves continuing for additional generations with additional rounds of mutagenesis. The appearance of phenotypically affected plants (e.g., albino seedlings) will increase as we proceed with iterative mutageneses and go into M4, M5 generations, onwards.

If the goal is to stop at BC2M3, then 100 Kernals from each lot can be planted and self-pollinated to generate BC2M3S1 families The resulting 2,500 families can be planted to phenotype the material but also to collect tissues and samples for sequencing to generate a sequence indexed resource for reverse genetics. In addition, other methods for detecting the presence of mutations can be used for reverse genetics, such as TILLing (US Pat. Pub. U.S. 20040053236 A1 for McCallum et al.).

Figure 3A:
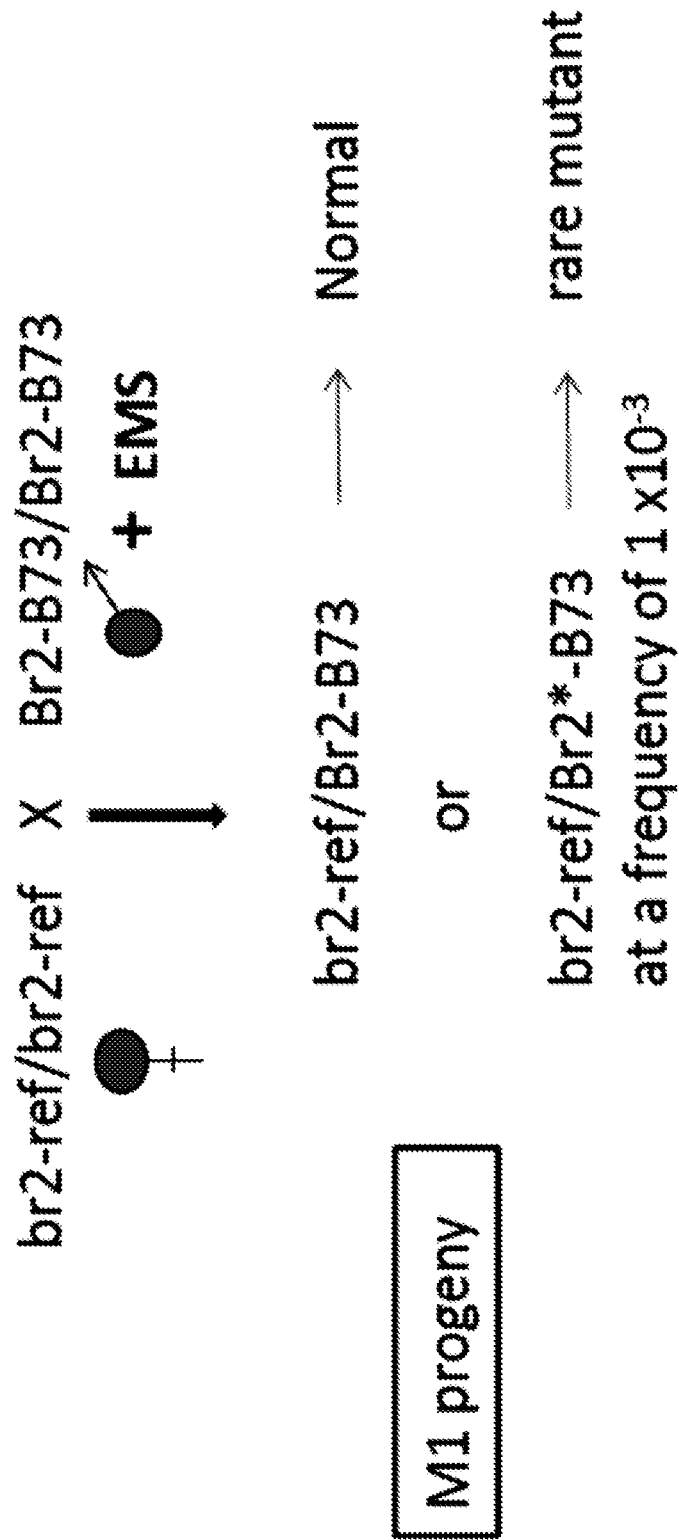
FIG. 3a is a plot showing mutagenesis using a chemical mutagen.
Figure 3B:
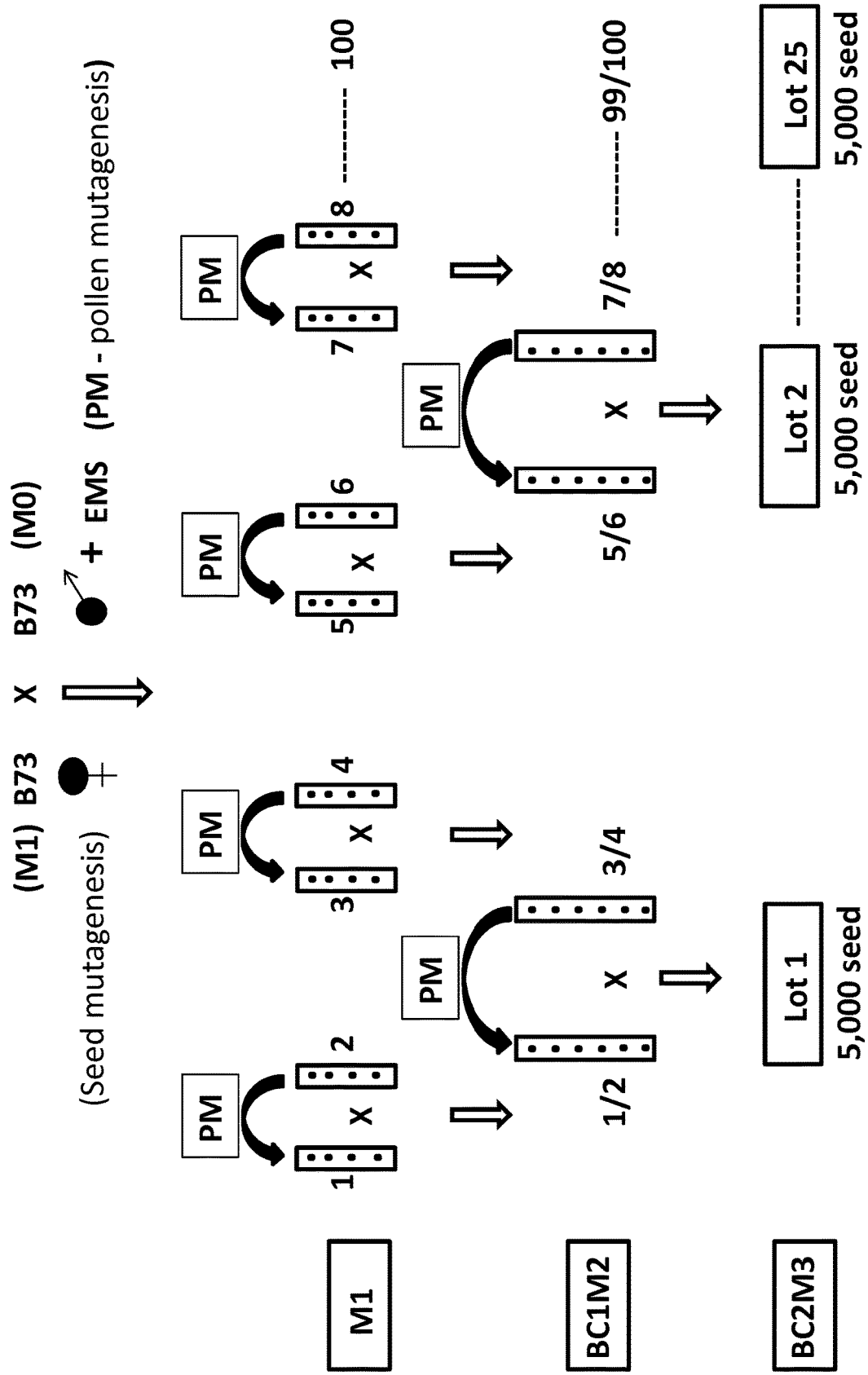
FIG. 3b is a plot showing mutagenesis using a chemical mutagen.

Referring to FIGS. 3a and 3b, in another embodiment, another round of chemical mutagenesis is applied. Seed mutagenesis is combined with pollen mutagenesis in the M1 generation to contribute mutagenized alleles through both parents and add at least one more round of mutagenesis. For example, the seed is first treated with EMS and then the resulting M1 plants are pollinated with EMS-treated pollen in one of the two ways. The first way involves taking fresh pollen from normal B73 plants (non-mutagenized), treat it with EMS and pollinate M1 ears to generate the BC1M2 seed. This seed has mutations from the female side as well as new mutations from the male side consolidated in a heterozygous condition. The second way involves collecting pollen from the M1 plants themselves and treating it with EMS before pollinating M1 ears with it. The resulting BC1M2 seed has 3 rounds of mutagenesis, one from the female side and two from the male. However, there is one key problem. It should be noted, however, that utilizing the second way, the seed-induced mutations will not stay independent in generations M2 and beyond if use the M1 pollen for the pollen EMS mutagenesis protocol.

It should be appreciated that the number of plots defined in FIG. 1 and in the above description are only presented as an example. The herein disclosed method may be scaled up as desired because the number of plots is defined by the number of crosses that are possible.

In the embodiment presented in FIG. 1, the maize seeds are not mutagenized. These "unmutagenized" seeds are planted and a plant is grown from which pollen is collected. The pollen is subjected to mutagenesis (via, e.g., EMS) to produce the M1 seed. This M1 seed is used to pollinate plants from independently mutagenized lines. In other embodiments, however, other options exist for the plants used in the initial cross. In an alternate embodiment, each of the plants in the first generation are derived from seeds which independently experience a round of chemical mutagenesis (e.g., via EMS). Then, a separate set of pollen derived from unmutagenized plants is itself subjected to chemical mutagenesis (e.g., via EMS), and is then used to pollinate the now mutagenized ear parents, thereby forming a F1M1 seed, instead of an M1 seed. Adding this step results in an increased number of mutant alleles. Thereafter, referring to FIG. 1, all of the subsequent steps involving the "M1 plant" can now be carried out with the F1M1 plant.

Another alternate embodiment involves maximally mutagenizing the parents, by starting out with mutagenized seed to generate the ear parents and also mutagenizing seed to produce the pollen parents. Then the pollen collected from plants resulting from mutagenized seeds is mutagenized as before and used to generate an F1M1. Thereafter, referring to FIG. 1, all of the subsequent steps involving the "M1 plant" can now be carried out with the F1M1 plant.

In another alternative embodiment, the ear parents (M0) remain unmutagenized but the pollen parents are derived from chemically mutagenized seeds. Pollen from the mutagenized plants is collected and subjected to chemical mutagenesis and used to derive the M1 progeny in crosses to the unmutagenized ear parents to produce the F1M1 plant referred to above. Thereafter, referring to FIG. 1, all of the subsequent steps involving the "M1 plant" can now be carried out with the F1M1 plant.

Yet another embodiment involves treating the M0 seed with a chemical mutagen (Ethyl Nitrosourea (ENU), for example, because it induces 3 to 3.5 fold more mutation compared to EMS) and then self-pollinating/sib-mating the ears of M1 plants with EMS-treated pollen from the same M1 plants to produce the M2 seed which may then be self-pollinated to produce M3 populations for forward or reverse genetic screens.

It should also be noted that the starting genetic material in any of these embodiments may be inbred, double haploid, the same as the crossing parents, or genetically distinct therefrom.

In yet another embodiment, the seed or pollen is treated with a mutagen different than EMS, which can be any chemical. A few that can be used are: ENU (N-ethyl-N-nitrosourea), NMU (Nitrosyl methyl urea), Methyl Methanosulfonate (MMS), Ethidium Bromide, psoralen, acridine orange, and Sodium Azide. Some of these cause single base pair substitutions. For example, ENU is specifically attractive. It produces not only A to T and T to A transversions but also all possible transitions. In contrast, EMS has a strong bias for GC to AT transitions. Any chemical that induces a mutation can be used in this process. Currently, EMS has been optimized in the pollen EMS mutagenesis protocol, leaving open the possibility that other mutagens may be tested to work with pollen.

In yet another embodiment, to enhance mutation frequency, following each pollen EMS mutagenesis, kernels are preferentially selected from those ears that were pollinated the last. Because the pollen that led to these Ks were in contact with EMS for a longer time, they harbor more mutations. Different doses of the EMS treatment or the duration of the EMS treatment may also be applied to attain the desired end mutation frequency.

In yet another embodiment, the often-encountered problems associated with mutational load of the pollen are avoided by preselecting kernels residing towards the tip of the ears. The silks of the ovules near the tip are much shorter than the silks of the ovules near the bottom of the ear and thus pollen competition is less in these kernels and heavily mutagenized pollen are more likely to successfully pollenate these ovules. Because the mutagenized pollen has to travel (through the silk) less to accomplish fertilization of the ovules near the tip of the ear, the mutational load of the EMS pollen may also be of a lesser problem as well.

In yet another embodiment, pollen toxicity of EMS is mitigated by constituents geared toward maintaining pollen viability such as antioxidants and nutrients. In yet another embodiment, low mutation frequency due to the robust DNA repair system of the maize pollen is controlled using reagents that impair DNA repair, such as 7-Nitroindole-2-carboxylic acid which acts as an inhibitor of base excision repair.

The embodiments presented above result in a library of point mutations with a greater mutation density per individual than what is possible with the current chemical mutagenesis approach. Another significant advantage of some embodiments of this approach is that they lead to a mutant library in the form of the BC2M3 that is almost immortal seed (125,000 is shown in FIGS. 2a and 2b but more can be created quickly from the BC1M2 seed by chemical mutagenesis) and can be planted at any time for any need by any researcher anywhere in the world. This resource can be saturated with point mutations, yet mutations can be propagated as in a heterozygous condition. This makes the aforementioned embodiments feasible. A portion of BC2M3 seed can also be self-pollinated and sequence indexed generate a highly effective and valuable resource G for reverse genetics. Thus the herein disclosed process lends perfectly to both forward and reverse genetics screens.

In another embodiment, a complementary approach can be taken. First, start with a seed and treat it with a mutagen to result in a treated seed. This mutagen can be EMS, another chemical or even a physical agent such as fast neutrons, gamma rays, x-rays or UV light. The treated seed (which is now considered the M1 seed) is then planted to grow M1 plants. These M1 plants are either self-pollinated or mated with each other in a one-to-one combination to produce the M2 seed. At this stage whether these M1 plants are selfed or crossed with each other, the consequences are the same (we are simply consolidating independent mutations from the ear and tassel lineages, so it does not matter whether these come from the same plant or different). The M2 seed from individual ears are kept apart from here on and are planted in different plots/rows. However, before planting they are treated with the same mutagenizing agent as before. The treated seed is now called M3 and the plants derived from it the M3 plants. Next, the M3 plants in adjacent plants are crossed with each other to produce M4 seed. This M4 seed has undergone 4 rounds of mutagenesis in just two generations.

In yet another embodiment, two more rounds of mutagenesis can be added to have six rounds of mutagenesis within just 2 generations. This can be achieved by adding a pollen EMS treatment step at each of the M1 and M3 levels described above. For example, pollen of M1 plants can be treated with EMS before attempting self or sib-matings between M1 plants. Similarly, pollen from individual M3 plots can be collected and treated with EMS before attempting to pollinate ears of the adjacent plot in a one-to-one combination. The advantage of this design is that one can accomplish the task in two years rather than in three. Also, one can mix two or more mutagens to enhance the spectrum of mutations because different mutagens has the potential to mutate different DNA bases.

Example 1

Figure 4:
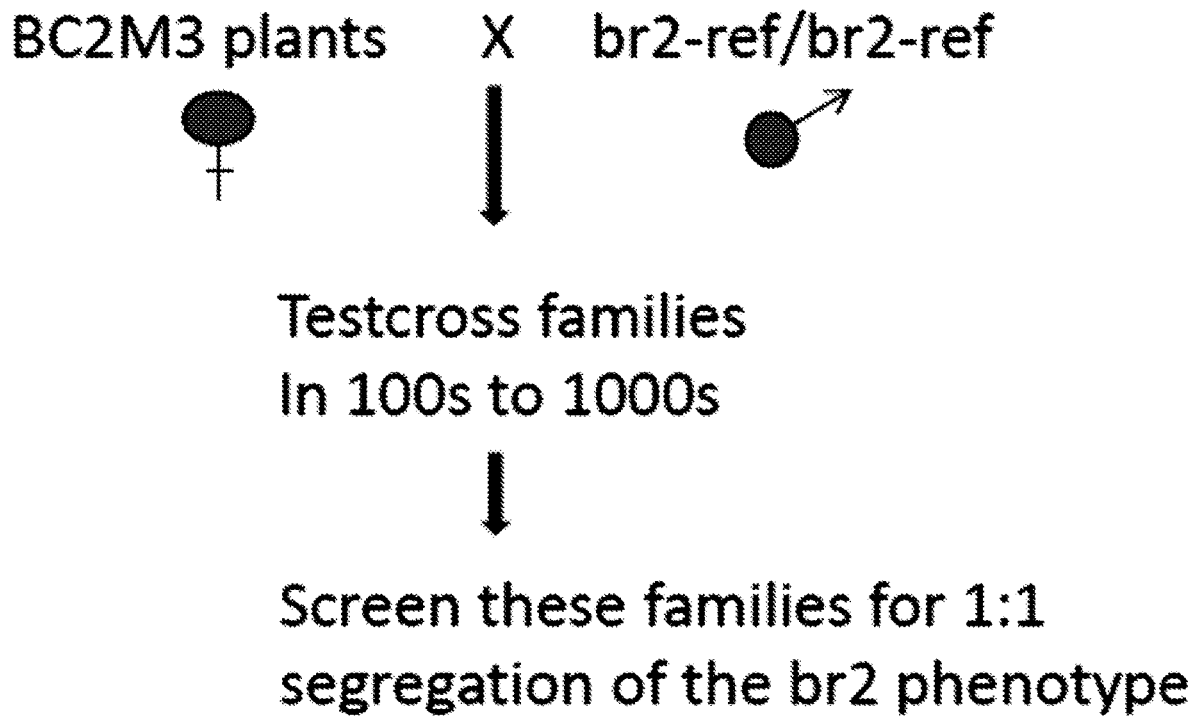
FIG. 4 is a process flow of the traditional approach to accomplish targeted mutagenesis.

Generating Allelic Series of Known Gene Mutations by Targeted Mutagenesis and Especially of Genes of Agronomic Importance that Benefit from Having Weak or Subtle Mutant Alleles:

An example that can be cited is of the dwarfing br2 mutation, which has the potential to allow redesigning of the corn architecture in ways that can help break yield barriers for this crop. The traditional approach to accomplish targeted mutagenesis is outlined in FIG. 4. The mutant tester is used as the female parent and is fertilized with the EMS-treated pollen from a wild-type inbred (for example, B73). A few thousand of the M1 progeny thus generated are planted and screened for INDIVIDUAL mutants with a short stature typical of br2. The procedure works reasonably well for alleles in which the function of the gene is disrupted more or less completely (i.e., the mutation is either fully null or almost null). The procedure is largely ineffective in providing partial loss-of-function mutations because of the difficulty of spotting such mutant individuals in the background of normal M1 plants. It is not uncommon to see many M1 plants that seem to have aspects of the mutant phenotype of interest but lack heritability (i.e., they are false positive). Despite best efforts using traditional approaches, it yields too many false positives, the consequence of which is that even if a genuine mutant is present among the collection it may not be possible to retrieve it.

Figure 5:
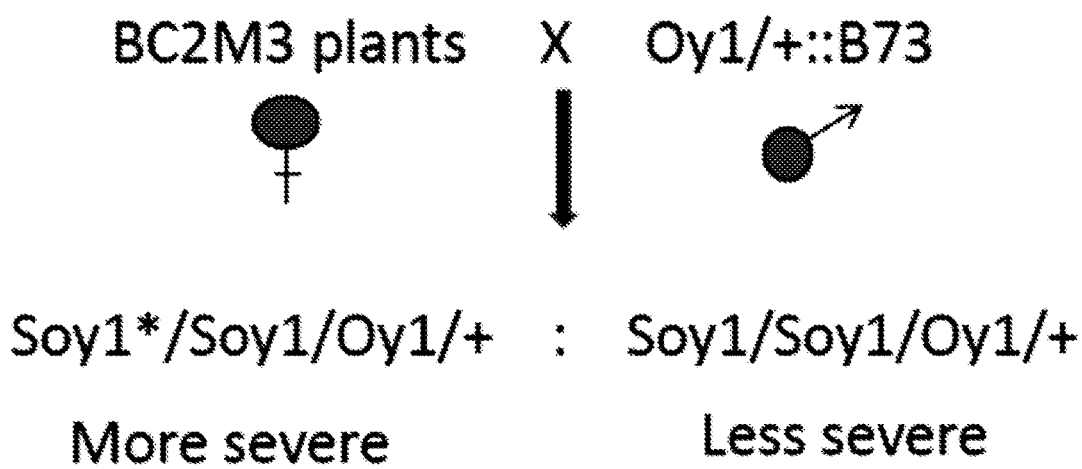
FIG. 5 shows a non-complementation screen of mutagenesis using a chemical mutagen.

The following statements help demonstrate the herein disclosed method's superiority over existing methods. To identify new alleles of br2, the pollen from a br2 mutant tester is collected in glassine bags and then sprinkled onto the ears of the BC2M3 plants one by one to accomplish quick pollination. Since the BC2M3 seed is expected to carry multiple mutations in all maize genes, about 50 seeds from each of the 25 BC2M3 seed lots are planted and their ears pollinated with the br2 pollen to generate testcross progenies (FIG. 5). The next step is to plant about 10 to 20 progeny from each of these testcrosses and screen for the br2 phenotype segregating in a 1:1 ratio. This ability to produce and observe new mutants segregating equally with the wild-type siblings in a testcross population is what makes the idea underlying the herein disclosed method especially attractive. Since a new br2 mutation is being screened for at the level of a family and not as an individual in an entire population, br2 mutants of all severity can be easily ascertained, whether dramatic or subtle. Any BC2M3 plant that carries an EMS-induced mutation in the br2 gene (in heterozygous form) can give rise to the testcross progeny that would segregate equally for normal and br2 mutant plants.

Because all other recessive mutations can be masked by the WT genes from the br2 tester, only the effect of br2 will be revealed, and it can also be in a largely wild-type background of identical hybrids. Seeing multiple cases of a given mutation segregating in a 1:1 ratio validates that the new mutation is a genuine one, and because one has the convenience to compare multiple mutant plants with multiple wild-type siblings in a given testcross progeny, even mutants with subtle phenotypes have the chance to be sighted or revealed. This method completely eliminates the problem of false positives that can or often plague the traditional non-complementation screens. The feasibility and effectiveness of the herein disclosed method, of course, depends on the mutational efficiency of the BC2M3 seed. It will be possible (cost effective) only if the mutation frequency/density is high, so that relatively fewer testcross progenies will need to be generated and evaluated in phenotypic screens.

The herein disclosed method also allows one to generate and maintain mutations of interest in a background of interest without having to go through the trouble of lengthy introgressions. For example, in the testcross progeny of a given BC2M3 plant with br2, a new allele of br2 is found. The progenitor of this BC2M3 plant can be recovered from the BC2M3 seed lots (FIG. 1) and propagated by self-pollination to generate homozygous br2 mutants.

To Mutagenize and Clone Genes Underlying QTL:

An example that can be used here is that of the QTL suppressor of oil-yellow-1 (Soy 1), which was identified in B73 on the basis of its ability to suppress the phenotype caused by the oil-yellow-1 (Oy1) mutation phenotype. Oy1 is a partially dominant mutation arising from a defect in a gene that encodes one of the three subunits of the Magnesium chelatase enzyme responsible for the first committed step in chlorophyll biosynthesis. Soy1 was identified by a Oy1-based mutant-assisted gene identification and characterization (MAGIC) screen of the IBM RILs. The data suggested that B73 has a relatively suppressible allele of soy1 that somehow dampens the phenotype of the Oy1 mutation. In contrast, Mo17 has a weak or Oy1-enhancing allele at the soy1 locus. One way to validate Soy1 and also to facilitate its cloning will be to use the herein disclosed method as described in FIG. 5. Since Soy1 appears to be a dominant QTL, it can be knocked-out or knocked-down by crossing the BC2M3 plants with pollen from a Oy1/+mutant and then screening the resulting testcross populations for enhancement of the Oy1 phenotype. Again, like with the non-complementation screens described in FIG. 5, the change in the Oy 1 phenotype is observed at the level of a testcross progeny of 10 or more plants in which Oy1 would segregate in a 1:1 ratio with the WT plants. If the Soy1 allele is hit by EMS in any of the plants of the BC2M3 material, it is expected to exhibit a relatively more severe Oy1 phenotype. Again, as phenotypic evaluations are done on a family basis, even subtle changes in the Oy1 phenotype are detectable. Multiple mutants of identical phenotype in the same family serves to validate that the mutant detected is a genuine one and not a false positive.

The above approach identifies dominant or partially-dominant modifiers. However, to look for recessive modifiers of Oy1, one needs to go to the next generation. It can be accomplished by crossing a mutant F1 with a wild-type (WT) sibling (not shown in FIG. 5 but half of the siblings in every testcross progeny will be WT) in each of the testcross progenies. This generates pseudo F2 populations in which Oy1 will segregate in a 1:1 ratio but all other genes especially those that are not linked to the Oy1 locus—will segregate as in a bona fide F2 population.

But if the desired QTL are in lines other than B73, similar BC2M3 material can be produced in any of these lines and used to create and identify mutations in the respective QTL. An example is that of a QTL from the inbred TX303 (one of the 26 NAM founder lines) that carries a QTL that dramatically enhances the autoimmune phenotype of an autoactive R gene mutant (Rp1-D21). This enhancing QTL (named hrm12) was identified by a MAGIC screen of a NAM subpopulation that was derived from a cross of TX303 with B73. MAGIC makes use of the phenotype of a mutant as a reporter to reveal the presence of genes/loci present in any line. All one needs to do is cross the mutant with the line or lines of interest and then evaluate the resulting progeny for up or down gradation of the mutant phenotype. MAGIC screens can be conducted with individual lines or with structured populations such as the RILs or NILs. The advantage with the structured populations is that one needs only to evaluate the phenotype of the reporter mutation in the testcross progenies, as the genotypic data is already available for many of these structured populations. It was from a MAGIC cross of Rp1-D21 with the B73×TX303 RILs that the autoimmunity enhancing QTL hrm12 was revealed to be contributed by TX303.

Therefore, to generate and identify mutations in hrm12, BC2M3 material can be generated in TX303 and crossed with Rp1-D21 in the B73 background. In the resulting testcross progeny of BC2M3 plants that sustained EMS induced mutations in hrm11, we expect the segregation of Rp1-D21 plants whose phenotype is more or less suppressed compared to the rest of the Rp1-D21 siblings. Again much of the benefit accrues from the fact that because of the enhanced mutation frequency of the material one can conduct phenotypic screens for mutations of interest at the level of a family. On the one hand it serves to validate the heritability of the mutant and on the other it completely eliminates the possibility of a false positive being selected as a genuine mutant.

To Conduct Enhancer/Suppressor Screens:

As an example: it is desired to identify modifiers of br2. Cross br2 with hundreds of BC2M3 plants and self a few F1 plants from each of the testcross progenies to generate respective F2 populations. Screen these F2 pops for changes in the br2 phenotype. Depending on the expressivity of the br2 mutant used in these crosses, both suppressors and enhancers could be identified. The procedure would work better if the br2 mutation is also in the B73 background and has a phenotype that is neither too severe nor too suppressed, but intermediate, because this will allow the detection of both the enhancers and suppressors of br2 in the same screen.

The Herein Disclosed Method can be Used to Detect Genes Involved in Heterosis:

Heterosis has been hugely important in corn breeding for almost a century now. Despite this, current knowledge of what underlies heterosis genetically remains unrealized. The herein disclosed method is able to resolve it genetically. One of the inbreds that exhibits rather dramatic heterosis with B73 is Mo17. So to explore what may be responsible for heterosis between these inbreds, hundreds of BC2M3 plants can be pollinated with Mo17 to generate the hybrid testcross populations. These testcross families can be phenotypically evaluated for reductions in the rate of growth, plant height, maturity, overall vigor of the hybrid progenies etc. If a gene involved in heterosis is inactivated by EMS, it will reveal as half of the plants in the corresponding testcross progeny exhibiting a reduction in any of the heterosis traits mentioned above. This cross will reveal heterosis associated genes from B73, but to reveal the heterotic gene complement contributed by Mo17, a BC2M3 resource will have to be generated from this inbred as well to be crossed with the B73 inbred. Pollinations can be done quickly by pooling pollen and dispensing a little bit on each ear using glassine bags.

The Herein Disclosed Method can be Used to Detect Overdominant Genes:

One theory that tries to explain heterosis assumes the contribution of overdominant genes in this trait. Overdominant genes are those that when present in a heterozygous form outperform either allele in a homozygous condition. Recently, it has been shown that these overdominant loci also express their superiority in a heterozygous condition with a loss-of-function allele. A helpful example of an overdominant mutant locus of the latter kind is that of the tomato SFT (Single flower truss) locus, which increased tomato yields by 60% in heterozygous condition. Given that the herein disclosed method strives to keep all the mutations in a heterozygous condition throughout the protocol, it would provide excellent opportunities to identify overdominant loci that might be present in the maize genome.

Generating Dominant or Partially Dominant Mutations:

Again, as the mutations are maintained in a heterozygous condition, and also displayed at the level of families at every stem following the M1 generation, the herein disclosed method is ideal for revealing many such mutations that may have a dominant or partially dominant phenotype.

The Herein Disclosed Method is Used to Create New Traits in Elite Materials:

These traits can be conferred either by dominant mutations or recessive. These traits can include leaf architecture, stalk architecture, maturity level or any other trait that may be impeding the performance of an otherwise highly desirable inbred. Using the populations from different stages of development described in the method disclosed herein, one can also screen the material for the creation by mutagenesis of new value added traits such as herbicide resistance and disease resistance.

Example 2

Figure 6A:
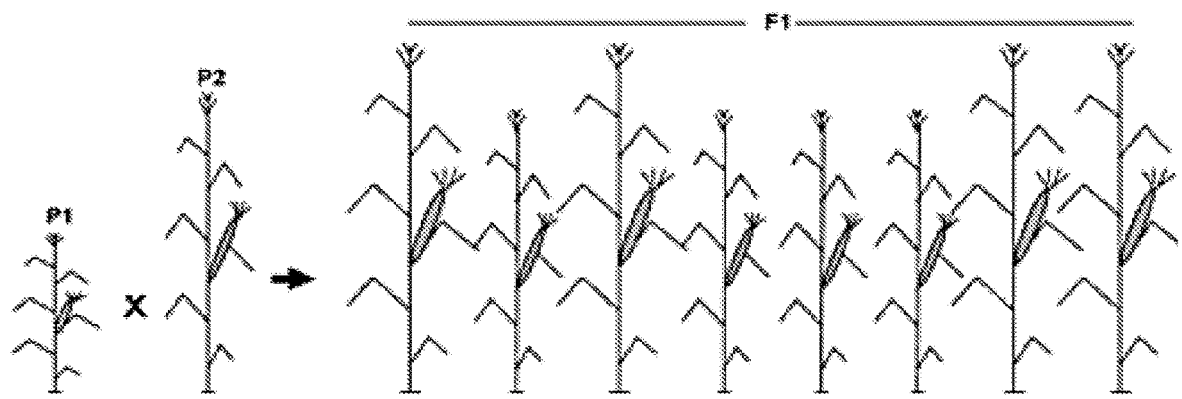
FIG. 6a is an illustration demonstrating the mutant-assisted gene identification and characterization (MAGIC) approach with a dominant reporter mutation, used as a heterozygote in an otherwise pure-breeding line (P1); P2 and P3 are two mapping population lines; F1 families segregate 1:1 for the mutation but are otherwise isogenic; the effect of the mutation is suppressed in the cross with P2.
Figure 6B:
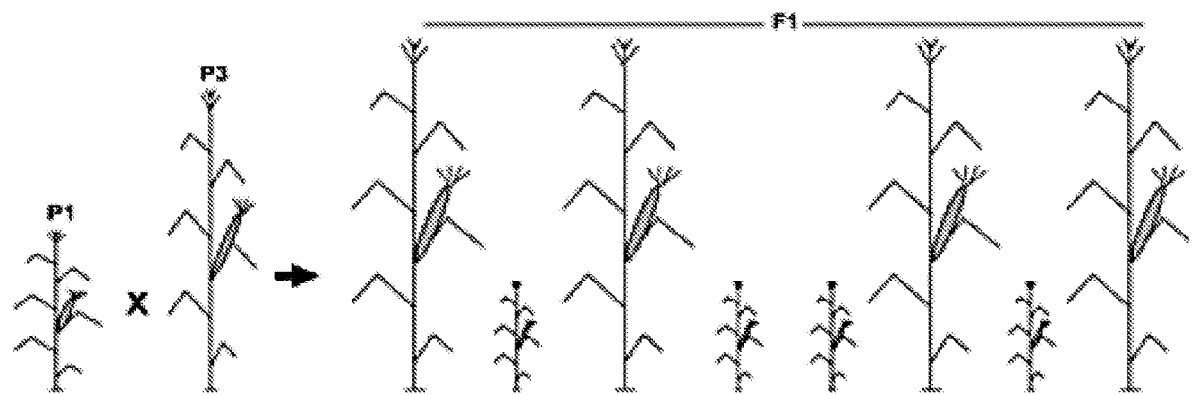
FIG. 6b is an illustration demonstrating the mutant-assisted gene identification and characterization (MAGIC) approach with a dominant reporter mutation, used as a heterozygote in an otherwise pure-breeding line (P1); P2 and P3 are two mapping population lines; F1 families segregate 1:1 for the mutation but are otherwise isogenic; the effect of the mutation is suppressed in the cross with P2 (FIG. 6a), relative to the P3 cross.

Mutant-Assisted Gene Identification and Characterization Approach:

The MAGIC technique uses an easily-observable mutant phenotype for a gene affecting the trait of interest as a reporter to discover and analyze relevant, modifier genes present in diverse germplasm. It involves crossing the mutant allele into diverse germplasm and evaluating the progeny for transgressive changes in the mutant phenotype(s). If the mutant allele is dominant, evaluations can be made immediately in the F1 generation. If the mutant is crossed to each line of a segregating mapping population, dominant and partially-dominant modifiers segregating in that population can be mapped in a straightforward manner (FIGS. 6a and 6b). Referring to FIGS. 6a and 6b, conducting MAGIC with a dominant reporter mutation, used as a heterozygote in an otherwise pure-breeding line (P1). P2 and P3 are two mapping population lines. F1 families segregate 1:1 for the mutation but are otherwise isogenic. The effect of the mutation is suppressed in the cross with P2 (FIG. 6a), relative to the P3 cross (FIG. 6b). Using the whole mapping population in this way allows for the straightforward identification of modifiers.

Figure 7:
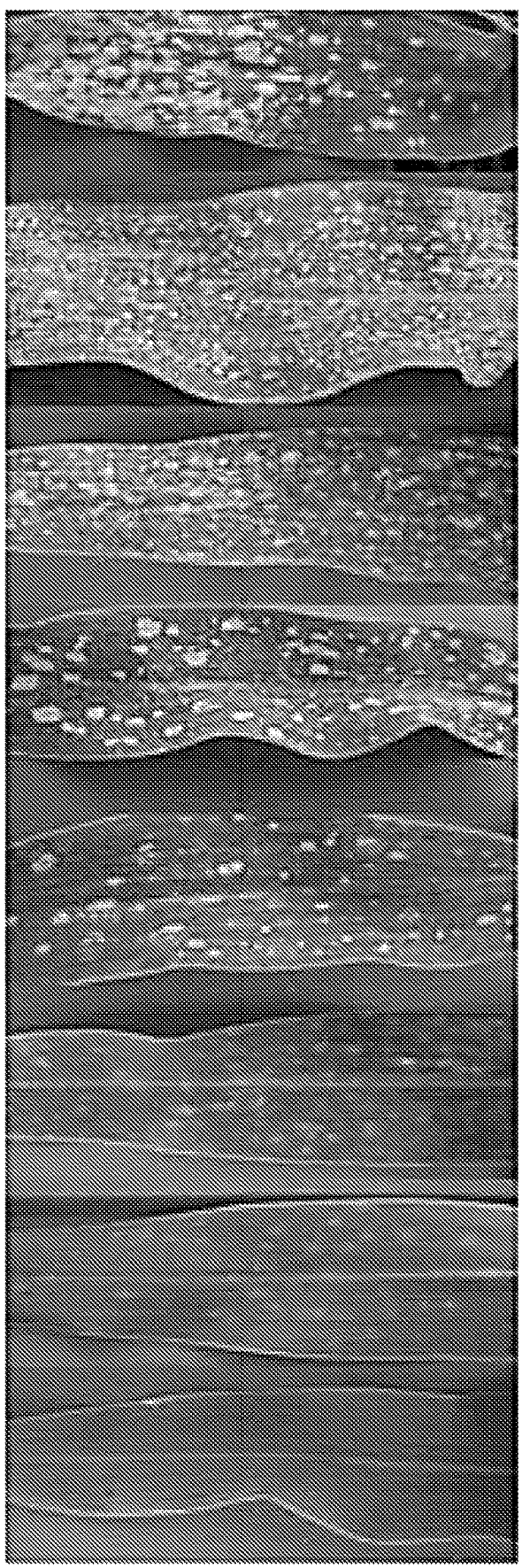
FIG. 7 contains photos showing the Rp1-D21 associated hypersensitive response (HR) phenotype varies when introgressed into diverse genetic backgrounds.

Hypersensitive response (HR) is a ubiquitous plant defense response, characterized by rapid, localized cell death at the point of attempted pathogen ingress. HR is generally induced by the products of dominant resistance (or R–) genes which initiate HR upon detection of specific pathogen-derived molecules. We used the MAGIC approach to investigate natural genetic variation responsible for controlling the maize HR. The dominant mutant phenotype was provided by Rp1-D21, a constitutively active ("autoactive") allele of the maize Rp1 common rust R-gene, which encodes a canonical NBS-LRR protein and causes the spontaneous induction of necrotic HR lesions in a pathogen-independent but genetic background-dependent manner (FIG. 7, which shows Rp1-D21-associated HR phenotype varies when introgressed into diverse genetic backgrounds). Rp1-D21 was originally identified as a chimera between two 'normal' NBS paralogs, Rp1-D and Rp1-dp2.

Modifiers of Rp1-D2/-induced HR were mapped in a number of populations including the intermated B73×Mo17 (IBM), Association and Nested Association Mapping (NAM) populations. In each case an H95 maize line carrying Rp1-D21 in a heterozygous state (designated Rp1-D21-H95) was crossed to the majority of the lines of the population. Mutant progeny from each cross were scored for a range of traits associated with severity of the HR phenotype. Using publicly available genotypic data, several quantitative trait loci (QTL) responsible for variation in these traits were mapped. Much of this has been published however our most complex and important experiment using the NAM population has only recently been completed and is under review for publication at the time of writing. For this work we crossed Rp1-D21-H95 to 3381 NAM lines and assessed the resulting F1 families with repeated checks in 4 environments. Joint linkage analysis was conducted to identify quantitative trait loci (QTL) using a linkage map based on more than 7000 SNP loci. Subsequently, GWA analysis using 26.5 million SNPs was conducted after adjusting for background QTL. GWA identified associated SNPs that colocalized with 44 candidate genes. These included five genes predicted to be involved in redox homeostasis, two in lignin biosynthesis, two in calcium signaling, 20 genes with predicted involvement in control of programmed cell death (PCD), autophagy, and/or ubiquitin-mediated protein degradation pathways and four in the defense response (Table 1). Twelve of the candidate genes were differentially expressed between NILs differing for the presence of Rp1-D21. Most of these regulatory and metabolic pathways had been previously associated with HR in some way. This example provides the first system-wide analysis of natural variation that modulates the HR response in plants.

TABLE 1

Selected candidate genes identified by GWA in the NAM population significantly associated with the Rp1-D21 HR phenotype

| Selected maize candidate genes | p-val[1] | Fold induction by Rp1-D21 | | Pathway |
| --- | --- | --- | --- | --- |
| | | B73 | Mo17 | |
| Candidate genes differentially expressed between mutant Rp1-D21 and wild type[2] | | | | |
| Hydroxycinnamoyl-CoA shikimate transf. | 33.3 | 296 | 224 | lig, dfr |
| UEV domain/VPS23/ELC | 21.5 | 8.4 | 6.9 | aut, ubq |
| IQ calmodulin-binding motif domain prot. | 13.9 | 2.2 | 4.2 | $Ca^{2+}$ |
| Caffeoyl-CoA O-methyltransferase | 8.4 | 2.2 | 1.7 | lig, dfr |
| Spotted leaf 11/plant U-box 13 | 8.9 | 2.2 | 2.5 | pcd |
| RP1/NB-ARC domain dis. resistance prot. | 11 | 0.7 | 2.3 | pcd, dfr |
| IQ calmodulin-binding motif domain prot. | 8.5 | 4.8 | 4.5 | $Ca^{2+}$ |

TABLE 1-continued

Selected candidate genes identified by GWA in the NAM population significantly associated with the Rp1-D21 HR phenotype

| Selected maize candidate genes | p-val[1] | Fold induction by Rp1-D21 | | Pathway |
|---|---|---|---|---|
| | | B73 | Mo17 | |
| Serine/threonine-protein kinase CTR1 | 8.8 | 4.2 | 5.4 | pcd, dfr |
| Pectin lyase-like superfamily protein | 11.8 | 1.9 | 2.2 | dfr |
| Lipoxygenase 3 | 8.5 | 3.8 | 5.7 | pcd, rxh |
| RING/U-box superfamily protein | 9.4 | 2.3 | 2.9 | pcd, ubq |
| Candidate genes not differentialy expressed between mutant Rp1-D21 and wild type | | | | |
| Modifier (Mod(r)) protein, VPS37 | 8.3 | | | aut, ubq |
| Cytochr. bd ubiquinol oxidase, 14 kDa sbunit | 11.6 | | | rxh |
| Jacalin-like lectin domain prot./CRK7 | 13.9 | | | pcd, dfr |
| Zinc finger C-x8-C-x5-C-x3-H type | 15.7 | | | dfr |
| RP1/NB-ARC domain dis. resistance prot | 11.5 | | | pcd, dfr |
| Calmodulin calcium sensor prot., OsCML30 | 14.5 | | | $Ca^{2+}$ |
| MATE efflux family protein, EDS5/SID1 | 7.4 | | | rxh, dfr |
| Carbamoyl phosphate synthetase B | 10.4 | | | pcd |
| Cystathionine b-synthase domain prot. | 14.2 | | | rxh |

[1]log10 of average p value from GWA analysis based on 100 resampling method;
[2](FDR < 0.2)
Key: Lignification: lig; Programed cell death: pcd; Autophagy, aut; Calcium signaling, $Ca^{2+}$; defense response, dfr; redox homeostasis, rxh; ubiquitination, ubg.

Figures 8A, 8B, 8C:
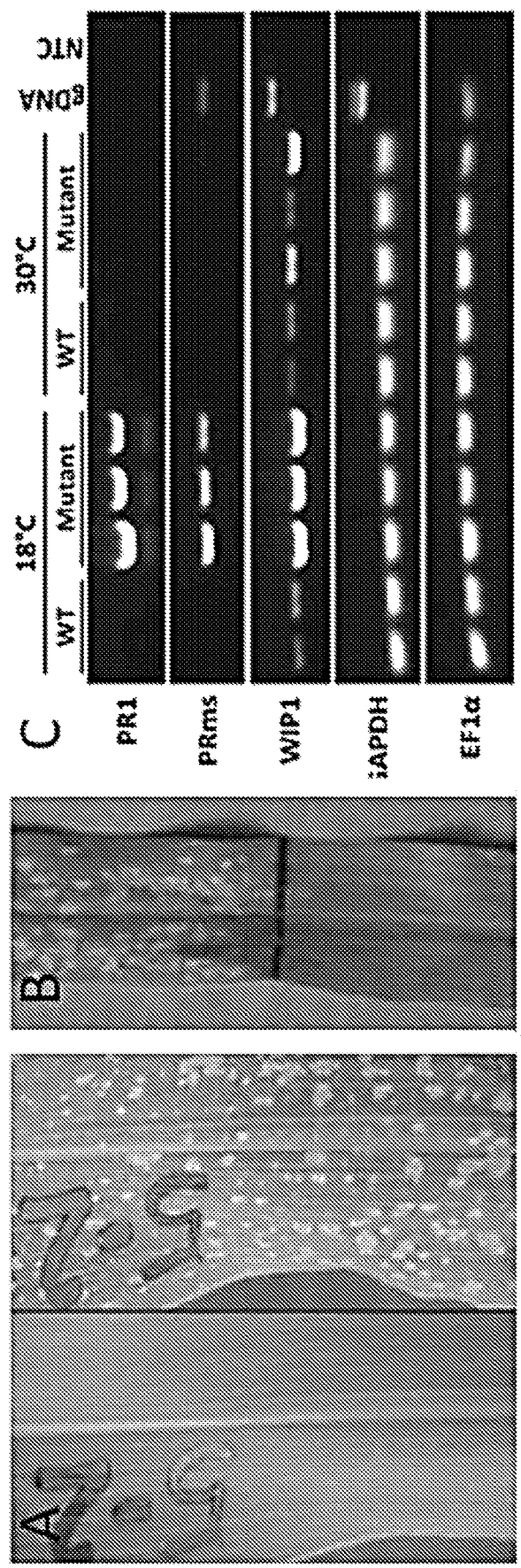
FIG. 8a shows that a line carrying Rp1-D21 showed no lesions after three weeks growth at 34/30° C. (left) but showed numerous lesions 48 hours after shifting to 22/18° C. (right).
FIG. 8b shows the lower section of the 4th leaf of a Tx303×Rp1-D21-H95 F1 plant grown at 34° C. which was wrapped in aluminum foil to exclude light and the temperature was changed to 22/18° C. for 48 hours; the leaf is shown immediately after foil removal.
FIG. 8c shows the expression of three maize genes associated with the defense response, PR1, PRms and WIP1 was measured using semi-quantitative PCR in three mutant two WT seedlings derived from the cross Tx303×Rp1-D21-H95.GAPDH and EF/awere included as reference genes; 30° C.: amplification of RNA extracted from the plants grown at a constant 30° C. for three weeks; 18° C.: amplification of RNA from the same plants after the temperature was dropped to a constant 18° C. for a further seven days.

It is shown that Rp1-D2/-induced HR was associated with several hallmarks of wild-type (WT) HR, including production of reactive oxygen species, induction of pathogenesis related genes and induction of salicylic acid (PBK unpublished) providing further evidence that the phenotype conferred by Rp1-D21 is indeed an exaggerated form of HR. Rp1-D21-induced HR was also shown to be both light- and temperature-dependent (FIGS. 8a 8c), a common feature of HR induced by R-genes. Importantly we were able to suppress Rp1-D21-induced HR at both phenotypic (FIG. 8a) and gene-transcription (FIG. 8c) levels when plants were grown at or above 30° C.

Example 3

Figures 9A, 9B:
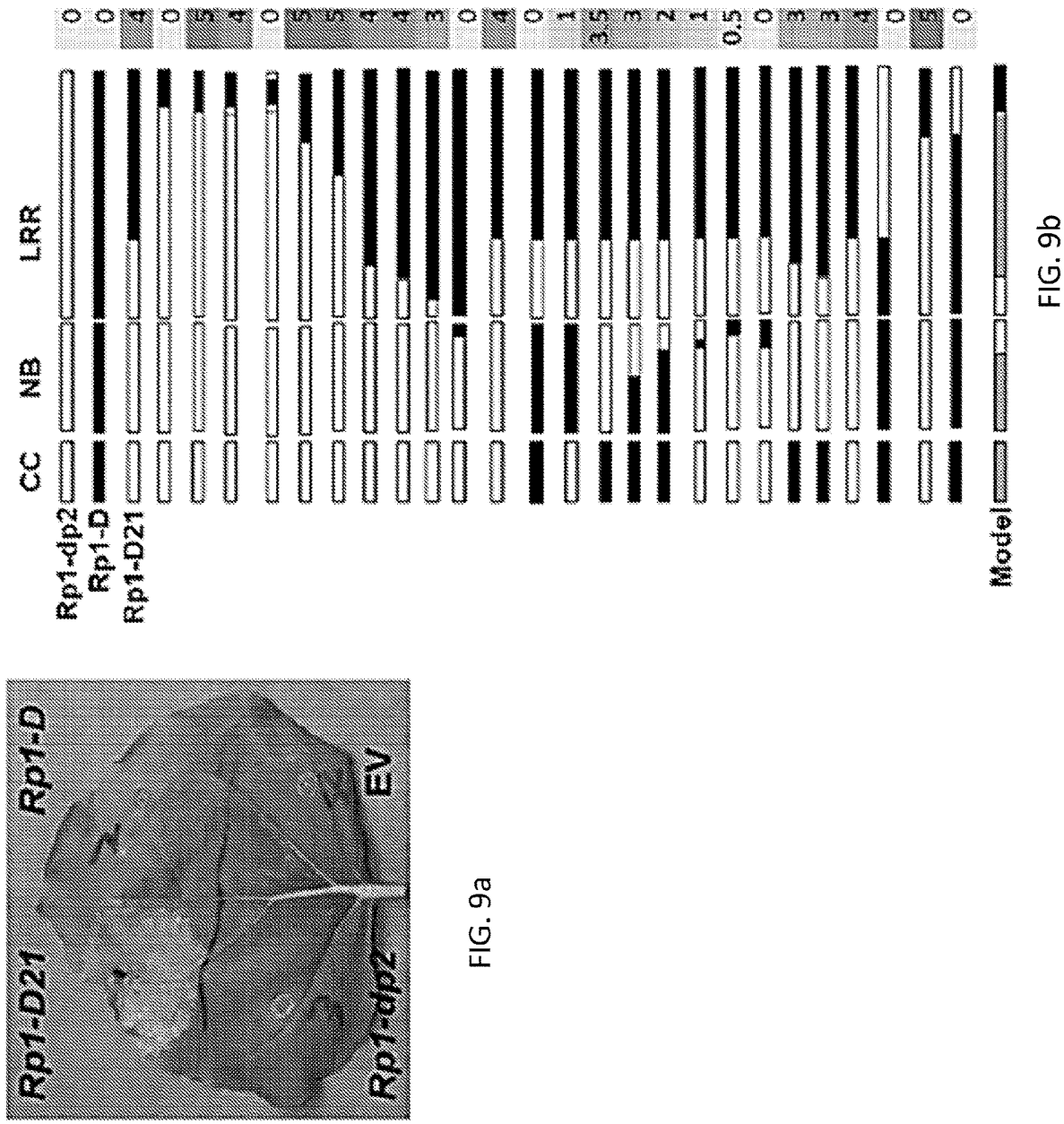
FIG. 9a shows transient expression of Rp1-D21 and its two parental alleles in N. benthamiana.
FIG. 9b is a schematic showing Rp1-D21 and its parental alleles (top) and recombinants between them and the results of their transient expression in N. benthamiana scored on a 0-5 scale (0=no HR, 5=full HR); a model showing the minimal regions required for auto-activity is shown at the bottom.

In another example, it is shown that the Rp1-D21 phenotype can be recapitulated and analyzed in *Nicotiana benthamiana* (FIGS. 9a 9b). HR was observed when Rp1-D21, but not either 'progenitor' allele Rp1-D or Rp1-dp2, was transiently expressed in *N. benthamiana* (FIG. 9a). We cloned fourteen Rp1-D21 loss-of-function point mutations from maize and transiently expressed four of these alleles in *N. benthamiana*; none conferred HR. Furthermore, the Hd2 allele of Rp1 which was previously shown to induce HR in transgenic maize, also induced HR in our transient expression system. Thus we recapitulated the maize HR phenotype conferred by Rp1-D21 and all six alternate alleles tested in this system. It is therefore appropriate for structure-function studies of Rp1-D21 activation, the identification and characterization of interacting proteins and characterization of variants.

Recombinant genes were constructed between mutant and parental alleles. Transient expression of these recombinant genes identified regions of Rp1-D21 necessary for autoactivity (FIG. 9b). These experiments also defined the role of a previously uncharacterized domain of NBS-LRR R-genes and showed that Rp1-D21 shuttles between the nucleus and cytoplasm to induce HR (data not shown). These data, combined with modeling simulations, generate a testable model for Rp1-D21 autoactivity.

Example 4

Figure 10:
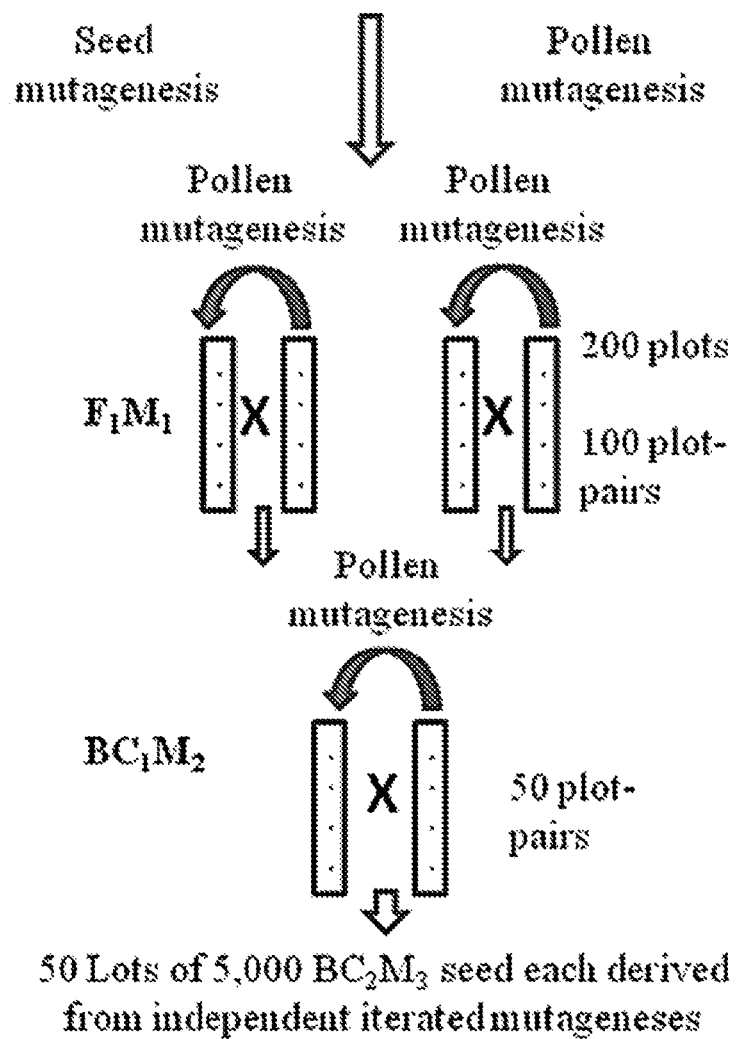
FIG. 10 is an example scheme for an aspect of the method disclosed herein.

As another example of the herein disclosed novel mutagenesis method dubbed NextGEM (for Next Generation EMS Mutagenesis), this method has four key features: Feature 1: Mutation density is increased over three-fold, by iterative rounds of mutagenesis and propagating mutations as heterozygotes (FIG. 10); Feature 2: A paired-row mutagenesis design produces an essentially immortal, reusable seed library in the form of BC2M3 seed highly enriched in mutations. This resource can be used for the analysis of any trait; Feature 3: Segregating families rather than individual plants are screened. Thus, any line harboring a putative mutation modulating the phenotype should be apparent in multiple individuals per family. Fewer false positives will be forwarded for analysis and more true positives can be detected than the individual plant approach. We can also validate and recover lost alleles by replanting a family; Feature 4: A genome-wide approach for mutant detection is used as opposed to a candidate gene approach. This allows the efficient discovery of new genes as well as the validation of existing targets.

The NextGEM approach is summarized in FIG. 10. Multiple rounds of mutagenesis using established techniques are combined with family-wise crosses. M1 plants from EMS-mutagenized seed plants are crossed with EMS-treated pollen from unmutagenized plants of the same line to produce F1M1 seed. In this example, F1M1 seed is planted in 200 plots. Crosses are made between neighboring plots by EMS-treating pollen to generate 100 lots of the BC1M2 seed. Crosses are again made between lots with a third round of pollen EMS-mutagenesis to produce 50 lots of BC2M3 seed with each lot containing independent mutations caused by four independent rounds of EMS mutagenesis.

It is known, from detecting quantitative trait loci (QTL) in F1 crosses between NAM RILs and Rp1-D21-H95 that there are multiple loci at which alleles with additive effects segregate to modify HR. In order to molecularly identify these alleles, it would be helpful to generate and screen variation in the lines from which these alleles are derived. We can generate NextGEM populations for a subset of NAM founders. Mutagenizing B97, M37W, Oh7b, Mo17, and Tx303. Rp1-D21 expressed in three of these lines (Mo17, M37W and Tx303) confers a relatively exaggerated HR phenotype and in the three others (B97, Oh7b, B73) the HR phenotype is relatively suppressed. This procedure generates a rich source of induced alleles in these NAM founder lines for any maize geneticist looking to screen for novel phenotypes or identify variation to permit cloning of QTL.

A sensitized screen is used to identify mutations capable of modifying the HR and then clone those mutations by sequencing using an informatics pipeline built for raw variant discovery. We identify mutations affecting HR by two strategies. First, we generate a NextGEM population from each of the aforementioned 6 NAM founder lines. For simplicity and specificity the example of B73 is described here, but all inbreds listed above can be mutagenized. A B73 BC2M3 NextGEM population of 50 pools can be generated (FIG. 10). Pollen from a B73 line into which Rp1-D21 has been introgressed (Rp1-D21-B73) can be applied to 30 BC2M3 plants from each pool and kernel from each resulting ear will be stored separately. Plots of 25 seed from each of 1500 ears can be grown and scored for HR. On average Rp1-D21 (segregating 1:1) and any mutation affecting HR (also segregating 1:1) should occur together in ¼ of the plants or about six times per plot. This permits multiple observations of each mutant genotype and avoids the problem of single plant screening. Families segregating for HR severity in both North Carolina and Indiana will be prioritized for cloning. These individuals will be crossed to produce segregating families for gene cloning and further characterization. Because our screening uses a congenic Rp1-D21 introgression as our test-cross line, only the variation induced by EMS and the segregation of the Rp1-D21 allele contribute to genetic variation in these materials. Thus, mutations with moderate effects on the HR will not be masked by QTL segregating in the background. This also enables the use of the EMS-induced variation as molecular markers to map and clone the mutations responsible for variation in HR by a highly efficient procedure. Furthermore, this screen is not complicated by intragenic modifiers in the Rp1-D21 gene itself, as the tester was not mutagenized.

A second strategy involves mutagenesis of material carrying the Rp1-D21 allele. Rp1-D21 limits female fertility in severe backgrounds and in homozygotes. We generate a NextGEM population using the B73 and A632 Rp1-D21 introgressions in which the HR phenotype is sufficiently suppressed to permit female fertility. In this case, each generation of the mutagenesis permits scoring for haploin-sufficient alleles conferring enhancement/suppression of the phenotype on a single plant basis. In these cases, backcrossing of a plant carrying a putative enhancer/suppressor to unmutagenized congenic Rp1-D21 can be performed to confirm the phenotype. At the BC2M3 generation we self all individuals and retain seeds from each ear separately. 25 seeds per ear can be planted and screened for suppression or enhancement of the HR. In this case mutations affecting HR severity should segregate in the population with the ratio (1:3, 3:1, 1:2:1) depending on the dominance relationships between the mutated and WT alleles. Mutants are crossed to congenic lines lacking Rp1-D21 to test for any mutations that may have occurred in the Rp1-D21 gene itself. Plots showing similar effects on HR in both locations unlinked to Rp1-D21 will be prioritized for cloning. These immortalized NextGEM populations have the substantial advantage of allowing the detection of recessive mutations.

Mapping and Cloning of Causal Variants:

The mutated genes thus generated can be molecularly identified by whole genome sequencing of bulked segregants within test-cross families. Sequencing and identifying EMS-induced alleles that cosegregate with the phenotype is not enough. We can construct populations and analysis pipelines so that one and only one potentially phenotype inducing mutation can be identified. False positive SNP calls dramatically limit the value of next generation sequencing data for rare variant discovery and mutant cloning. By using the sequence data from independently-mutagenized lines as biological replicates of the error-prone positions we have removed 75% of called SNPs in a population of sequenced Sorghum mutants. This allowed us to catalog the true function-perturbing mutations in each line. We can apply this same approach here. Approximately 300 non-synonymous, 20 twenty gene-disruption (e.g. nonsense, splice site) and more than 10,000 silent-site or non-coding mutations per individual can be expected. This SNP density is more than sufficient to map the region of the genome responsible for a change in the HR. The novel congenic Rp1-D21 crossing strategy allows the EMS-generated polymorphisms in a line to serve as molecular markers to distinguish the causative mutation from the other 299 potentially functional polymorphisms.

Cloning Dominant Modifiers of the HR:

Progeny from crosses between mutagenized lines to unmutagenized congenic Rp1-D21 introgression lines are used for this screen. In plots with putative mutants, all WT individuals will be crossed to congenic Rp1-D21 testers and all modifier mutants with Rp1-D21 can be crossed to unmutagenized respective wildtypes. 100 seed of each F1 family will be planted and phenotyped for HR. For each family, we will collect tissue from 12 Rp1-D21 individuals with the most extreme modified phenotypes and from 12 plants with unmodified Rp1-D21 phenotypes. For each mutant, a mutant and WT bulk will be sequenced to a minimum depth of 20×. SNPs will be called after alignment to the B73 reference genome and sequentially filtered for quality, coverage, and absence of that SNP in independently mutagenized material. Only the heterozygous GC to AT SNPs that make up >99% of the EMS-induced alleles will be retained for analysis. All protein coding sequence changes can be cataloged.

With ~300 protein coding sequence changes and 1500 centiMorgans we need only map to 5 cM resolution to distinguish causative from linked protein coding variation, and we will exceed this resolution. All intergenic and silent site SNPs between each of non-synonymous SNP will be treated as a bin. All sequencing reads at known EMS-induced SNP sites will be counted. This turns the average 33 silent SNPs between each nonsynonymous SNP into a marker sequenced to 660× depth. This more than suffices to map to one and only one polymorphism responsible for the mutant phenotype given the number of chromosomes that make up each bulk. The region of the genome containing the modifier of the HR will be devoid of EMS-induced SNPs in the unmodified Rp1-D21 bulks and be 1:1 EMS-induced SNP to reference allele in the mutant bulk. Candidate polymorphisms will be confirmed by genotyping individual mutants and wildtypes in segregating populations by PCR (e.g. KASPAR markers) to demonstrate co-segregation. Further characterization of homozygous phenotype of the modifier, recessive phenotypes, morphological effect, comparison to mapped QTL and GWAS SNPs, and QTL testing in crosses to H95 Rp1-D21 will be undertaken. By utilizing crosses of the modifier mutants back to the parent genotype we accomplish two massive efficiency increases. First, we do not introduce segregation variance in our mapping cross and can more precisely assess genotype to phenotype relationships in our materials. Secondly, we know that the crossing partner only introduces reference alleles at EMS-induced SNP positions. A proof of concept of this approach in Sorghum successfully cloning visible mutants by this approach has been conducted.

Cloning Recessive Modifiers of the HR:

The recessive mutants identified by NextGEM of Rp1-D21 homozygotes will be cloned by a different strategy. For each modifier mutant, DNA is isolated from mutant individuals and they are selfed and crossed to the respective homozygous Rp1-D21-B73 or –A632 introgression. The F1 plants are crossed to selfed mutant progeny to generate BC1F1 families segregating 1:1 for the mutant phenotype, offering the best statistical power for the fewest number of plants. 100 BC1F1 individuals will be grown per cross and the 25 best representatives for modified and unmodified Rp1-D21 HR phenotypes will be selected and DNA isolated as bulks. DNA from the two bulks and original mutant individual will be sequenced at a minimum depth of 7×. This provides 14× coverage for the causative SNP (when combining the BC1F1 mutant pool and mutant individual reads) and sufficient depth for mapping using the silent sites. SNPs will be called by comparison to the B73 reference genome and filtered for sequence quality, coverage, and SNPs present in independently mutagenized material. Homozygous GC to AT SNPs in the mutant individual sequence will be cataloged. These positions will be scored for allele frequency in the two bulks. At the location of the causative mutation, EMS induced alleles should approach homozygosity in the mutant pool and should drop to 50% in the unmodified bulk. Again, all intergenic and silent site SNPs between each coding sequences will be binned to use phenotypically-neutral EMS SNPs between each coding sequence as markers, in this case sequenced to 231× depth for each bulk. The sequence of the mutant bulk and mutant individual will be digitally pooled and homozygous GC to AT SNPs called. Any of these SNPs present in the WT bulk, or any other sequence data will be removed. Candidate polymorphisms that fit the criteria for the causative mutation (there should be one and only one by this procedure) will be genotyped in at least 50 individuals from segregating populations (e.g. KASPAR markers) to eliminate possible sources of bias, confirm the mutation, and demonstrate cosegregation of the mutation and phenotype. Further characterization of phenotypes, morphological effects, and linkage to QTL and GWA candidates are possible. Since we will generate genome-wide information about potentially causative alleles from the sequence of the mutant individual this suffices for positional cloning. Even moderate-effect alleles that would be lost in the noise by any other method can be cloned by this procedure. This includes the NextGEM BC2M3 for B73, Mo17, Tx303, M37W, B97 and Oh7B.

The NextGEM population offers an unprecedented capacity to detect these alleles. The population generated in the first NextGEM approach can also be extended to reveal recessive modifiers. If enough Rp1-D21 modifiers are not observed, a few WT plants from each of the testcross progenies can be sib-mated with the Rp1-D21 mutant siblings to produce sib-mated F2 populations in which the Rp1-D21 phenotype would segregate 1:1 but the rest of the genome (unlinked to Rp1-D21) would segregate as in a F2. These populations can be planted in replicated trials to screen for recessive mutations that enhance or suppress the Rp1-D21 phenotype and genes cloned by the approach described for recessive mutants.

It should be appreciated that the herein disclosed methods can be applied to a variety of seeds and crops, including those that are polyploid. This includes wheat, soybean, barley, maize, brassica, cotton, oats, potato, tomato, banana, watermelon, sugar beet, cassava, sugarcane. In addition cereal-type crops and rice.

Those skilled in the art will recognize that numerous modifications can be made to the specific implementations described above. The implementations should not be limited to the particular limitations described. Other implementations may be possible.

REFERENCES

1. Johal, G. S., P. Balint-Kurti, and C. F. Weil, *Mining and Harnessing Natural Variation: A Little MAGIC*, Crop Science, 2008. 49(6): p. 2066 2073.
2. Balint-Kurti, P. J. and G. S. Johal, *Use of Mutant-assisted Gene Identification and Characterization (MAGIC) to Identify Useful Alleles for Crop Impmrovement ISB News Reports*, 2011, January 2011: p. 1-3.
3. Chaikam, V. et al., *Use of mutant-assisted gene identification and characterization (MAGIC) to identify novel genetic loci that modify the maize hypersensitive response*, TAG Theoregical and Applied Genetics, 2011, 123(6): p. 985-997.
4. Bird, R. M. and Neuffer, M. G. 1987. Induced Mutations in Maize. Plant Breeding Reviews 5: 140-180.
5. Candela H[1], Hake S. 2008. The art and design of genetic screens: maize. Nat Rev Genet. 9(3): 192-203.
6. Hake, S., G. Neuffer, and G. S. Johal. 2008. The Mutants of Maize. In: *The Maize Handbook—Volume II: Domestication, Genetics and Genomics*. S. Hake and J. Bennetzen (Eds.).
7. Henikoff S[1], Comai L. 2003. Single-nucleotide mutations for plant functional genomics. Annu Rev Plant Biol. 54: 375-401.
8. Neuffer M G, Ficsor G. 1963. Mutagenic Action of Ethyl Methanesulfonate in Maize. Science. 139(3561): 1296-7.
9. Page D R[1], Grossniklaus U. 2002. The art and design of genetic screens: *Arabidopsis thaliana*. Nat Rev Genet. 3(2): 124-36.
10. Schy W E, Plewa M J. 1985. Induction of forward mutation at the yg2 locus in maize by ethylnitrosourea. Environ Mutagen. 7(2):155-62.
11. Till B J[1], Reynolds S H, Weil C, Springer N, Burtner C, Young K, Bowers E, Codomo C A, Enns L C, Odden A R, Greene E A, Comai L, Henikoff S. 2004. Discovery of induced point mutations in maize genes by TILLING. BMC Plant Biol. 28: 4:12.
12. Tsai H[1], Missirian V, Ngo K J, Tran R K, Chan S R, Sundaresan V, Comai L. 2013. Production of a high-efficiency TILLING population through polyploidization. Plant Physiol. 161(4):1604-14.

The invention claimed is:

1. A method for creating a desired genetic variant from a plant, the method comprising:
   a. subjecting isolated pollen to a chemical mutagen and a reagent to impair DNA repair to produce a first generation seed;
   b. planting the first generation seed in (n) plots to produce first generation plants;
   c. recovering mutagenized pollen from the first generation plants;
   d. pollinating a female parent of said first generation plant with the recovered mutagenized pollen to produce a next generation seed;

e. subjecting pollen from the next generation seed to mutagenesis to pollinate the first generation plant, resulting in a new next generation seed;
f. planting the new next generation seed to produce a new next generation plant; and
g. subjecting pollen from the new next generation plant to mutagenesis to pollinate the new next generation plant.

2. The method of claim 1, the reagent to impair DNA repair acts as an inhibitor of base excision repair.

3. The method of claim 1, the reagent to impair DNA repair is 7-Nitroindole-2-carboxylic acid.

* * * * *